(12) United States Patent
Causse (10) Patent No.: US 10,213,330 B2
(45) Date of Patent: Feb. 26, 2019

(54) ORTHOPAEDIC DEVICE FOR A LOWER LIMB OF A HUMAN, FOOTWEAR AND PROSTHESIS PROVIDED WITH SUCH A DEVICE

(71) Applicant: Benoit Causse, Pibrac (FR)

(72) Inventor: Benoit Causse, Pibrac (FR)

( * ) Notice: Subject to any disclaimer, the term of this patent is extended or adjusted under 35 U.S.C. 154(b) by 308 days.

(21) Appl. No.: 14/651,939

(22) PCT Filed: Dec. 13, 2013

(86) PCT No.: PCT/FR2013/053073
§ 371 (c)(1),
(2) Date: Jun. 12, 2015

(87) PCT Pub. No.: WO2014/091171
PCT Pub. Date: Jun. 19, 2014

(65) Prior Publication Data
US 2015/0320581 A1    Nov. 12, 2015

(30) Foreign Application Priority Data
Dec. 14, 2012   (FR) ..................................... 12 62103

(51) Int. Cl.
*A61F 5/01*    (2006.01)
*A43B 7/14*    (2006.01)

(52) U.S. Cl.
CPC .............. *A61F 5/0127* (2013.01); *A43B 7/14* (2013.01); *A61F 5/0111* (2013.01); *A61F 5/0113* (2013.01); *A61F 2005/0179* (2013.01)

(58) Field of Classification Search
CPC .... A61F 5/0111; A61F 5/0127; A61F 5/0113; A61F 5/019; A61F 5/14; A61F 5/0109;
(Continued)

(56) References Cited

U.S. PATENT DOCUMENTS 3,680,549 A * 8/1972 Lehneis ................ A61F 5/0111
602/23
4,441,265 A    4/1984 Burns et al.
(Continued)

FOREIGN PATENT DOCUMENTS

DE        95 326 C      3/1897
DE     85 34 733 U1    1/1988
(Continued)

OTHER PUBLICATIONS

Heel (n.d.) Farlex Partner Medical Dictionary. (2012). Retrieved May 17, 2017 from http://medical-dictionary.thefreedictionary.com/heel.*
(Continued)

*Primary Examiner* — Alireza Nia
*Assistant Examiner* — Rachel Berezik
(74) *Attorney, Agent, or Firm* — Young & Thompson (57) ABSTRACT

An orthopedic device for a lower limb of a human, includes: a front segment (2) suitable for receiving the sole of a forepart; and a rear segment (10) suitable for receiving the lower surface of the heel, wherein: the front segment and the rear segment consist of two separate parts, the front segment and the rear segment are connected by at least one resilient upper arch (8) which extends above the front segment and the rear segment, providing a recess for receiving the foot, and is suitable for maintaining the front segment and the rear segment in an inoperative position, such as to enable a relative movement of the front segment and the rear segment relative to one another, from the inoperative position, and to resiliently return the segments to the inoperative position thereof.

13 Claims, 4 Drawing Sheets

(58) Field of Classification Search
CPC .. A61F 5/30; A61F 5/32; A61F 5/0585; A61F 5/0102; A61F 5/0195; A61F 5/013; A61F 5/0118; A61F 5/05866; A61F 5/05858; A61F 5/05; A61F 5/0106; A61F 13/045; A61F 13/064; A61F 13/065; A61F 13/066; A61F 13/067; A61F 13/068; A61F 13/06; A61F 13/08; A61F 2013/00119; A61F 2013/00102; A61F 2013/00093; A43B 7/1405; A43B 7/141; A43B 7/144; A43B 7/18; A43B 7/19; A43B 7/20; A43B 7/22; A43B 7/14

See application file for complete search history.

(56) References Cited

U.S. PATENT DOCUMENTS

| | | | | |
|---|---|---|---|---|
| 4,476,858 | A * | 10/1984 | Curtis | A43B 5/00 602/23 |
| 4,637,381 | A | 1/1987 | Jungmann | |
| 4,674,487 | A * | 6/1987 | Schaeffer | A45D 44/02 602/22 |
| 5,088,479 | A * | 2/1992 | Detoro | A61F 5/0113 602/27 |
| 5,658,241 | A | 8/1997 | Deharde et al. | |
| 5,718,673 | A | 2/1998 | Shipstead | |
| 6,083,184 | A | 7/2000 | Kenosh | |
| 6,592,539 | B1 * | 7/2003 | Einarsson | A61F 5/0109 602/26 |
| 6,945,947 | B2 * | 9/2005 | Ingimundarson | A61F 5/0113 128/882 |
| 9,186,270 | B2 * | 11/2015 | Blanck | A61F 5/0111 |
| 2005/0240139 | A1 * | 10/2005 | Bushby | A43B 7/142 602/61 |
| 2007/0038169 | A1 * | 2/2007 | Alon | A61F 5/0111 602/27 |
| 2010/0324461 | A1 | 12/2010 | Darby et al. | |
| 2011/0088145 | A1 | 4/2011 | Harada | |
| 2011/0203137 | A1 * | 8/2011 | Long | A43B 5/12 36/91 |
| 2011/0314591 | A1 * | 12/2011 | Mitsuno | A61F 13/08 2/239 |
| 2012/0123309 | A1 * | 5/2012 | Toenges | A61F 5/0111 602/27 |
| 2015/0374529 | A1 * | 12/2015 | Summit | A61F 5/0118 602/22 |

FOREIGN PATENT DOCUMENTS

| | | |
|---|---|---|
| FR | 2 953 126 A1 | 6/2011 |
| JP | H08191849 A | 7/1996 |
| WO | 2009144967 A1 | 12/2009 |

OTHER PUBLICATIONS

Sole (n.d.) Farlex Partner Medical Dictionary. (2012). Retrieved May 17, 2017 from http://medical-dictionary.thefreedictionary.com/sole.*

Plate. (n.d.) Oxford Dictionary. Retrieved May 24, 2017 from https://en.oxforddictionaries.com/definition/plate.*

Resilient. Oxford Dictionary Online, definition 2, https://en.oxforddictionaries.com/definition/resilient.*

International Search Report, dated Apr. 22, 2014, from corresponding PCT application.

* cited by examiner

ORTHOPAEDIC DEVICE FOR A LOWER LIMB OF A HUMAN, FOOTWEAR AND PROSTHESIS PROVIDED WITH SUCH A DEVICE

BACKGROUND OF THE INVENTION

Field of the Invention

The invention relates to an orthopaedic device for a lower limb of a human. The invention also relates to an orthopaedic device of this kind which further comprises a leg part. The invention also relates to a shoe equipped with an orthopaedic device of this kind as well as to a prosthesis equipped with an orthopaedic device of this kind.

An orthopaedic device according to the invention is useful for people who experience difficulties in walking, for example people who are affected by central and peripheral neurological disorders such as paralysis of the leg and foot, or even people who are affected by certain diseases of the muscles. An orthopaedic device according to the invention is also useful for people who are experiencing traumatic or non-traumatic joint symptoms, or certain amputations.

Description of the Related Art

Throughout the text, "orthopaedic device" is understood to mean any device which is intended to support a lower limb of a human and/or to mitigate functional deficiencies of a lower limb of a human or, possibly, any device which is intended to replace, at least partially, a lower limb of a human.

Walking is a complex mechanism which involves numerous muscles belonging to the whole of the human body. In this mechanism, the lower limbs have to bring about both stabilisation and propulsion of the body.

The walking cycle of each lower limb of a human comprises a supporting phase and a rocking phase. The supporting phase comprises all the stages during which the foot is in contact with the ground. The rocking phase comprises the stages during which the foot is not in contact with the ground, thus enabling the lower limb to move forward.

At the start of the step during the rocking phase, the leg is displaced forwards in relation to the other leg, in the suspended state, until the heel comes into contact with the ground, thus obtaining an initial support. The supporting phase comprises a first stage with the heel supported on the ground (taligrade contact), a second stage with the sole of the foot supported (plantigrade support), and then a final stage with the forefoot and toes, particularly the big toe, supported (digitigrade support). Thus, at the end of the step, the loss of contact between the foot and the ground takes place, physiologically speaking, at the big toe.

Steppage is one of the most common walking disorders, and one whose causes may be very diverse. It may be encountered constitutionally, in the case of acquired or congenital illnesses and in the context of pathologies such as diseases of the muscles, Charcot-Marie-Tooth diseases, the Guillain-Barré syndrome, multiple sclerosis, or hemiplegias of a central origin resulting from a cerebral vascular problem, or following various accidental injuries. It consists in a defect in the levator muscles of the foot which affects or prevents dorsiflexion (a bending movement of the foot towards the top of the body). Thus someone whose foot is dropping or dangling is obliged to lift the leg in an exaggerated manner at the start of the step so as to avoid his/her forefoot touching the ground during the rocking phase of walking.

In order to remedy these problems, an ankle brace forming a cradle for receiving the foot is known, for example (U.S. Pat. No. 6,083,184). An ankle brace of this kind comprises a sole which extends under the foot, from the ankle to the toes, a part which surrounds the ankle and a zone for fastening the brace onto the upper part of the ankle. An ankle brace of this kind does not enable movements to be accompanied dynamically when walking, its role being purely a static one.

FR 2 953 126 proposes a dynamic brace comprising a sole for the foot and a band for the leg which are connected by a structure comprising an elastic cylinder behind the leg and the foot. Actuation of the cylinder enables the sole to pivot about the ankle joint in such a way as to lift the foot at the end of the step.

A dynamic brace of this kind makes it necessary to add complex additional devices, and requires regular adjustments on the part of the medical staff after being fitted on a patient. Moreover, a dynamic brace of this kind does not make it possible for movements to be accompanied in a satisfactory and sufficiently dynamic manner when walking, nor to provide a physiological propulsive effect which is specific to human bipedalism at the end of the step.

BRIEF SUMMARY OF THE INVENTION

The object of the invention is therefore to mitigate these drawbacks and to propose an orthopaedic device for a lower limb of a human which makes it possible to:
  mitigate deficiencies in the levator muscles of the foot;
  provide a lifting effect at the start of the step when walking;
  provide a propulsive effect at the end of the step when walking, or possibly running;
  provide a stabilising effect, and in particular a lateral stabilisation effect, for a lower limb of a human, especially during the various phases of walking or running;
  keep the foot in a position which is normal and suitable for walking;
  promote muscular recovery by specific and appropriate stimulation of the muscles of the lower limbs of humans, particularly after an accident or in the case of an illness which affects the muscles of the lower limbs, and especially the levator muscles of the foot; and
  wear said device, if necessary, in a shoe, especially a sports shoe, a formal shoe or an orthopaedic shoe, and particularly in a shoe which keeps the ankle in position.

The object of the invention is also to propose an orthopaedic device which has the advantage of having low invasiveness and being ergonomic (light and non-bulky) for the patient.

In order to accomplish this, the invention relates to an orthopaedic device for a lower limb of a human comprising:
  a front segment which is adapted to receive the sole of a forefoot;
  a rear segment which is adapted to receive the lower face of the heel of said foot;
  wherein:
  the front segment and the rear segment are formed from two pieces which are distinct from one another;
  the front segment and the rear segment are connected by at least one resilient upper arch which;

extends above the front segment and the rear segment, providing a recess for receiving the foot;

is adapted to keep the front segment and the rear segment in an inactive position; and is adapted to make possible a relative displacement of the front segment and rear segment in relation to one another, starting from the inactive position, and to bring back the front segment and the rear segment resiliently into the inactive position.

An orthopaedic device according to the invention is adapted to receive a foot, the forefoot and the heel of the foot resting, respectively, on the front segment and the rear segment of the device, these latter being kept in position and connected resiliently by an upper arch.

The front segment and the rear segment are formed from two pieces which are distinct from one another, that is to say from two distinct segments which are not formed from the same continuous segment nor connected to one another in the same plane (in the inactive position), unlike a continuous sole which extends under the entire lower surface of the arch of the foot. In other words, the front segment and the rear segment are formed from two pieces which are distinct and distant from one another in a longitudinal direction of the foot, and distinct and distant from one another in a plane which comprises a longitudinal direction of the foot and is perpendicular to a sagittal plane (that is to say, a plane which is parallel to the lower surface of the arch of the foot).

An orthopaedic device according to the invention consists, in particular, of a brace for a lower limb of a human. The orthopaedic device according to the invention may also, in certain cases, constitute a prosthesis for at least part of a lower limb of a human, the brace then being associated, for example, with a foot prosthesis and/or leg prosthesis.

Throughout the text, "forefoot" is understood to mean the front part of a foot, including the toes and the five metatarsal bones.

An orthopaedic device according to the invention makes it possible to keep the foot in an anatomically appropriate position when in the inactive position, for example when standing up, as well as during any other movement of the lower limb, especially the movements associated with walking or running, without impeding them. An orthopaedic device according to the invention is thus suitable for accompanying the foot in its movements while at the same time exerting a force for bringing the front and rear segments back to the inactive position, owing to the upper arch.

The inventor discovered, surprisingly, that, unlike especially a sole in the form of a flexible plate, an orthopaedic device according to the invention provides not only the maintenance of the foot in an anatomically correct position, in particular in the inactive position, especially in the static position, for example when standing up, but also a propulsive dynamic effect at the end of the step, after the manner of a spring or a resilient bow which restores kinetic energy (in the form of a throwing-forward of the foot at the start of the rocking phase) having stored up resilient potential energy (through the effect of the weight of the body resting on a foot).

The inventor also discovered, surprisingly, that an orthopaedic device according to the invention makes it possible to mitigate the deficit in the muscles of the lower limbs of humans and, in particular, in the pedal muscle (or short extensor muscle of the toes), the role of which would seem essential to the walking mechanism. In actual fact, the inventor was able to discover a major improvement in the functioning of the pedal muscle, the latter appearing to play the part of an active tension-sensor which controls the other muscles surrounding the ankle.

This energy-restoring mechanism, which makes it possible to restore or improve the impulse towards a new step at the end of a step, resides in the presence of at least two distinct segments, the front segment and the rear segment, which are connected resiliently by the upper arch.

Moreover, the inventor was able to discover that an orthopaedic device according to the invention is particularly effective as a re-educative tool after an injury or surgery when the pedal muscle is functionally inadequate or inactive. The orthopaedic device according to the invention can be used in cases of ankle sprains, tendinitis or torn tendons (in particular the Achilles tendon) or algodystrophies and in the aftermath of surgical operations on the foot and lower limb. The orthopaedic device according to the invention makes it possible to provide an impulse which has become inadequate in such cases, and thus to bring the step and its development into line with a motor pattern which is not static but dynamic.

It should be noted that the front segment is formed from a first piece and the rear segment is formed from a second piece, the said first piece and the said second piece being distinct from one another, that is to say distinct and distant from one another in a plane which is parallel to the lower surface of the arch of the foot. An orthopaedic device according to the invention therefore does not have a continuous sole that extends under the entire lower surface of the arch of the foot.

The front and rear segments may have any shape which is suitable for supporting the sole of the forefoot and the heel, respectively. In particular, advantageously and in accordance with the invention, the front segment is formed from a first plate and the rear segment is formed from a second plate which is distinct (and distant) from the first plate.

Since the rear segment is adapted to receive the heel and to be disposed under the latter, and the front segment is adapted to receive the forefoot and to be disposed under the latter, the rear and front segments are disposed in the longitudinal (and in particular sagittal) prolongation of one another. In actual fact, the front segment and the rear segment extend, advantageously and in accordance with the invention, in the longitudinal prolongation of one another and are longitudinally spaced apart from one another, at least in the inactive position.

Apart from at least one upper arch, the front segment and the rear segment are, advantageously and in accordance with the invention, neither integral, nor connected continuously, with one another in a plane which receives the lower face of the foot after the manner of a sole. On the contrary, the front segment and the rear segment are, advantageously and in accordance with the invention, connected resiliently to one another exclusively by at least one upper arch above the foot.

Thus displacements of the front segment and the rear segment in relation to one another are made possible, in particular, both in, by and large, the longitudinal direction of the foot (which is also a sagittal direction) and in a direction which is orthogonal to the longitudinal direction of the foot, in the sagittal plane.

Displacements of the forefoot and the heel of a foot which is equipped with an orthopaedic device according to the invention, especially when walking or running, are therefore allowed.

In actual fact, each upper arch is adapted, advantageously and in accordance with the invention, to make possible a relative displacement of the front segment and the rear segment in relation to one another, starting from the inactive position in a sagittal plane and, by and large, in the longitudinal direction of the foot.

At each relative displacement of the front segment and/or the rear segment in relation to the inactive position, the upper arch(es) exert(s) a force for bringing the front segment and/or the rear segment back into the inactive position.

Each upper arch extends above the front segment and the rear segment and in such a way as to be capable of connecting them resiliently and of keeping them in the inactive position or of bringing them back to the inactive position after being displaced by the forces exerted on the front segment and the rear segment by the feet, the dynamic forces of walking, and the weight of the body.

Several modes of embodiment of the invention are possible as regards the number, shape, dimensions, materials and relative dispositions of the upper arch or arches. An orthopaedic device according to the invention advantageously comprises an upper arch which extends, obliquely and in contact with the upper face of the foot, between a lateral end of the front segment and a lateral end of the rear segment. In particular, the upper arch extends between a lateral end of the front segment and a lateral end of the rear segment in such a way as to wind round, and in contact with, the foot, after the manner of a portion of a helical bandage or of a strip which is wound round on itself. More particularly, each arch is adapted to pass above, and close to, the instep, especially at the base of the five metatarsal bones and/or at the five metatarsal bones.

In one particularly advantageous variant of embodiment of the orthopaedic device according to the invention, the upper arch extends between an outer lateral end of the front segment and an inner lateral end of the rear segment.

In this way, the orthopaedic device forms a structure which is continuous from the inner end of the front segment as far as the outer lateral border of the rear segment.

The front segment is adapted to receive at least part of the lower face of the forefoot, and to be disposed opposite and underneath at least part of said lower face of the forefoot. The front segment thus extends under at least one metatarsus of the foot in such a way as to at least partially support the lower face of the forefoot and to be capable of exerting a force for bringing said forefoot back to the inactive position when a relative displacement of the segments out of the inactive position occurs.

In particular, the front segment is, advantageously and in accordance with the invention, adapted to receive the big toe of the foot. Said front segment is therefore adapted to be disposed, especially, opposite and underneath the lower face of the big toe of the foot. When the wearer is standing up or during the supporting phases of walking or running, the big toe therefore rests on the front segment of an orthopaedic device according to the invention. Thus during walking, when the foot is bent while resting on the ground on the big toe with the heel raised in relation to the ground, the resilient upper arch makes it possible to propel the foot dynamically forwards, that is to say to move on into the rocking phase.

In one advantageous variant of embodiment of an orthopaedic device according to the invention, the front segment extends transversely between an inner lateral edge which is adapted to receive the big toe and an outer lateral edge which is adapted to receive the fifth metatarsus of the foot, in particular the region situated close to the little toe and especially the region close to the head of the fifth metatarsal (in front of the phalanx of the little toe). The front segment is thus disposed in such a way as to extend under the entire width of the foot and to provide optimum support for the forefoot.

The rear segment is adapted to receive at least part of the lower face of the heel, and to be disposed opposite, and below, at least part of said lower face of the heel, in such a way as to support, at least partially, said lower face of the heel and to be capable of exerting a force for bringing back the rear part of the foot to the inactive position when a relative displacement of the segments out of the inactive position occurs.

In one advantageous variant of embodiment of an orthopaedic device according to the invention, the rear segment extends transversely between an inner lateral end and an outer lateral border, in such a way as to extend under the entire width of the heel.

In one advantageous variant of embodiment, an orthopaedic device according to the invention makes it possible to support not only the forefoot and the heel but also the arch of the foot. This support is particularly important when the walking problem is accompanied by sagging of the arch of the foot or even in cases where the foot collapses. An orthopaedic device according to the invention advantageously comprises an appendage which is adapted to receive the arch of the foot and, in particular, to form a support for said arch.

The upper arch has, advantageously and in accordance with the invention, an appendage which is adapted to extend opposite the arch of the foot. This appendage is adapted, in particular, to extend in contact with the arch of the foot, especially when the foot is in the inactive position.

In one particularly advantageous variant of embodiment of an orthopaedic device according to the invention, the upper arch has an inner appendage which extends laterally and downwards and which is disposed longitudinally between the front and rear segments in such a way as to form a support for the arch of the foot. The said inner appendage of the upper arch is disposed on the inner side of the foot and is adapted to receive an inner lower median edge of the foot. The said inner appendage may especially extend under the foot, at least over a portion of the width of the foot, for example as far as half the width of the foot or advantageously under almost the entire width of the foot in such a way as to provide a larger surface for receiving the arch of the foot.

An orthopaedic device according to the invention may be adapted to be capable of being worn inside a shoe, especially a closed shoe, without needing any additional fastening device.

In one particularly advantageous variant of embodiment of an orthopaedic device according to the invention, the front segment has an inner lateral border which is adapted to support the big toe of the foot laterally. Such an inner lateral border of the front segment consists in a vertical prolongation of the said first plate. It makes it possible to keep the foot in an anatomically correct position inside the shoe and avoids, in particular, lateral deflection of the forefoot within the shoe.

In one variant of embodiment of an orthopaedic device according to the invention, the rear segment comprises a heel appendage which extends upwards and is adapted to receive the rear face of the heel. The said heel appendage is adapted to extend from the rear segment towards the leg and the calf, for example in the form of a heel collar, in such a way as to form a cup which is adapted to receive the heel. A heel appendage of this kind makes it possible to improve the maintenance of the foot in position within the orthopaedic device and to stabilise said foot during the various walking phases, especially the start of the step when resting on the ground with the heel.

In another variant of embodiment of an orthopaedic device according to the invention, said device comprises a portion which is adapted to be in contact with the instep, the said portion being connected resiliently to the rear segment.

An orthopaedic device according to the invention thus has a part which is called the "lower part" and is adapted to receive and support the foot. Said lower part comprises at least the front segment, the rear segment and the upper arch. The orthopaedic device according to the invention can be used when composed solely of this lower part.

As a variant, an orthopaedic device according to the invention comprises a lower part of this kind which is prolonged by a part, called the "leg part", which extends upwards, starting from the lower part (towards the leg and possibly as far as the thigh). Thus, in one particularly advantageous variant of embodiment of the invention, the orthopaedic device further comprises an upper segment which is adapted to receive at least part of the leg of the said lower limb of a human.

Throughout the text, "leg" is understood to mean that part of each lower limb of a human which extends from the knee to the foot.

Throughout the text, "front compartment" is understood to mean that part of the leg which contains the front tibial muscle, the big toe's own extensor muscle, the long extensor muscle of the toes and the front fibula.

Throughout the text, "outer compartment" or "lateral compartment" is understood to mean that part of the leg which contains the long and short fibular muscles.

Thus, throughout the text, "front outer compartment" or "front lateral compartment" is understood to mean that part of the leg which contains the muscles of the front compartment and the muscles of the outer (or lateral) compartment.

Throughout the text, "rear compartment" is understood to mean that part of the leg which contains the triceps muscle, the long flexor muscle of the big toe, the long flexor muscle of the toes and the rear tibial muscle.

The upper segment is adapted to extend in contact with at least a part of the leg that is wearing the orthopaedic device. In one particularly advantageous variant of embodiment of an orthopaedic device according to the invention, the upper segment is adapted to extend, at least partially, in contact with the front compartment of the leg.

Thus the upper segment of an orthopaedic device according to the invention does not extend solely in contact with the rear compartment of the leg, like a levator device which is known from the prior art, but also in contact with the front compartment of the leg.

An orthopaedic device according to the invention comprises an upper segment having at least one portion which is adapted to form a front support which is in contact with the front compartment of the leg.

In particular, an orthopaedic device according to the invention comprises an upper segment which:
  extends above the rear segment, providing a recess for receiving the leg; and
  has:
    at least one portion which is adapted to form a front support which is in contact with the front compartment of the leg, and
    at least one portion which is adapted to form a rear support which is contact with the rear compartment of the leg, the said upper segment being connected resiliently to the rear segment in such a way as to:
  keep the rear segment in the inactive position;
  make possible a relative displacement of the upper segment and the rear segment in relation to one another, and to bring back the upper segment and the rear segment resiliently into the inactive position.

The upper segment is, advantageously and in accordance with the invention, connected resiliently to the rear segment in such a way as to make possible a relative displacement of the upper segment and the rear segment in relation to one another in a sagittal plane.

The upper segment makes it possible to improve the maintenance of the lower limb in position by reinforcing the effect that keeps the foot in position, while at the same time making possible dorsiflexion of the leg towards the foot (about the axis of the ankle). The support formed by the upper segment about the leg which is wearing the orthopaedic device makes it possible to improve the forefoot-lifting effect of the orthopaedic device and, above all, to amplify the propulsive effect provided by the orthopaedic device at the end of the step.

Since the upper segment extends between at least one portion forming a front support which is in contact with the front compartment, and especially the front lateral compartment, of the leg and at least one portion forming a rear support which is in contact with the rear compartment of the leg, it also makes it possible to improve the lateral stabilisation of the foot and the leg, both in the static position and during walking or running, by helping to keep the leg and the foot in position in the same sagittal plane.

The leg part comprises, advantageously and in accordance with the invention, an opening/closing device which extends around said lower limb of a human.

In the same way, an orthopaedic device according to the invention may also comprise at least one portion which is adapted to form a front support which is in contact with the instep and makes it possible to amplify the propulsive effect provided by the orthopaedic device at the end of the step.

In one variant of embodiment of the invention, the leg part of an orthopaedic device according to the invention comprises an upper portion which extends upwards in such a way as to extend above the knee of the said lower limb of a human. The orthopaedic device according to this variant of the invention may thus form a cruro-pedal brace which is especially useful in cases of traumatic acquired or congenital muscular deficiencies of the leg.

An orthopaedic device according to the invention, whether or not supplemented by a leg part, may be formed from any material which is adapted to form the lower part which is capable of supporting the foot, with the front segment and the rear segment according to the invention connected resiliently by at least one upper arch. An orthopaedic device according to the invention may, in particular, be formed from any material chosen from among metal materials, polymeric materials and composite materials with a polymeric and/or metal matrix.

In particular, an orthopaedic device according to the invention is formed from any material which has improved behaviour in respect of fatigue, so as to withstand repeated deformations to which it is subjected during use (deformations which are linked to the movements of the foot and the leg, particularly when walking).

In one particularly advantageous variant of embodiment of an orthopaedic device according to the invention, said device is formed all in one piece. In particular, an orthopaedic device according to the invention is formed entirely from a single moulded unit. It is thus formed from the same material which is fashioned into a continuous structure which is adapted to support the lower limb and to transmit efficiently the forces to which the orthopaedic device is subjected. Thus the front segment, the arch and the rear segment are, advantageously and in accordance with the invention, formed from the same material which is fashioned into a continuous structure which is adapted to transmit the forces exerted on the various parts of the orthopaedic device during walking or any movement of the foot.

The choice of the same constituent material for forming the front segment, the arch and the rear segment at one and the same time also has the advantage of simplifying the method and the cost of manufacturing the orthopaedic device.

Furthermore, the inventor has realised that it is possible to produce an orthopaedic device of this kind which is light and non-bulky, while at the same time having adequate support and mechanical strength, by forming a main mechanical structure (which defines the static and dynamic mechanical behaviour of the orthopaedic device) by means of a polymeric composite material comprising fibrous reinforcements.

The orthopaedic device comprises, advantageously and in accordance with the invention, a main mechanical structure which is formed from a composite material comprising at least one reinforcement in the form of fibres and at least one polymeric material within which said fibres extend. The said main mechanical structure of the orthopaedic device is, advantageously and in accordance with the invention, formed from a composite material comprising woven or non-woven fibres and at least one polymeric material within which said fibres extend. Each reinforcement in the form of fibres is chosen, for example, from among carbon fibres, aramid fibres and glass fibres. The polymeric material within which the fibres extend is chosen from among the thermosetting polymeric materials and the thermoplastic polymeric materials which are suitable for making an orthopaedic device according to the invention. The polymeric material is chosen, for example, from among the epoxy resins or even the vinylester resins.

The said main mechanical structure is, advantageously and in accordance with the invention, a preformed thin strip—especially comprising at least one helical portion—made of rigid composite material which is resilient in flexion. If the orthopaedic device is intended to be disposed inside a shoe or used on its own, this resilient rigid strip is advantageously supplemented, on the inner side which is intended to come into contact with the patient, by at least one layer of padding material, especially a thin layer of polymeric foam which is chosen from the group made up of polyurethane foams, polyether foams and polyethylene foams.

An orthopaedic device according to the invention having a main mechanical structure formed from composite material with a polymeric matrix has the advantage of being thin, and is therefore adapted to be capable of being worn in a shoe, particularly in sports shoes or formal shoes.

An orthopaedic device according to the invention which also has a leg part is adapted to make possible all the relative movements of the foot, ankle and leg which are normally associated with standing, walking and running, that is to say the movements which are normally made possible by the ankle joint. The pedal part and the leg part are, advantageously and in accordance with the invention, adapted to form an angle of between 60° and 120° between them.

The invention extends to a shoe equipped with an orthopaedic device according to the invention. The invention therefore also relates to a shoe equipped with an orthopaedic device for a lower limb of a human comprising:
  a front segment which is adapted to receive the sole of a forefoot of a foot;
  a rear segment which is adapted to receive the lower face of the heel of said foot;
  wherein:
  the front segment and the rear segment are formed from two pieces which are distinct from one another;
  the front segment and the rear segment are connected by at least one resilient upper arch which;
    extends above the front segment and the rear segment, providing a recess for receiving the foot;
    is adapted to keep the front segment and the rear segment in an inactive position; and
    is adapted to make possible a relative displacement of the front segment and the rear segment in relation to one another, starting from the inactive position, and to bring back the front segment and the rear segment resiliently into the inactive position.

The orthopaedic device with which such a shoe is equipped may also have an upper segment as defined previously. In one advantageous variant of embodiment, an upper segment of this kind has a portion which is adapted to form a front support which is in contact with the instep.

Any type of shoe, in particular any type of closed shoe, for example a high shoe which is adapted to keep the ankle in position, can be equipped with an orthopaedic device according to the invention. The orthopaedic device is inserted in the shoe in such a way as to be disposed between the foot and the inner recess of the shoe. A shoe equipped with an orthopaedic device according to the invention therefore makes it possible to optimise the efficiency of a pedal brace according to the invention by improving the maintenance of the foot in position while at the same time being more aesthetic and more practical for protecting the foot from the external environment.

The invention extends to a prosthesis for at least one portion of a lower limb of a human, which prosthesis is equipped with an orthopaedic device according to the invention. Said invention therefore also relates to a prosthesis for at least one portion of a lower limb of a human, the said prosthesis being equipped with an orthopaedic device comprising:
  a front segment which is adapted to receive the sole of a forefoot;
  a rear segment which is adapted to receive the lower face of the heel of said foot;
  wherein:
  the front segment and the rear segment are formed from two pieces which are distinct from one another;
  the front segment and the rear segment are connected by at least one resilient upper arch which;
    extends above the front segment and the rear segment, providing a recess for receiving the foot;
    is adapted to keep the front segment and the rear segment in an inactive position; and
    is adapted to make possible a relative displacement of the front segment and the rear segment in relation to one another, starting from the inactive position, and to bring back the front segment and the rear segment resiliently into the inactive position.

The said prosthesis is, advantageously and in accordance with the invention, equipped with an orthopaedic device according to the invention comprising an upper segment which extends above the rear segment, providing a recess for receiving the leg, and has:

at least one portion which is adapted to form a front support which is in contact with the front compartment of the leg, and at least one portion which is adapted to form a rear support which is contact with the rear compartment of the leg, the said upper segment being connected resiliently to the rear segment in such a way as to:

keep the rear segment in the inactive position;

make possible a relative displacement of the upper segment and the rear segment in relation to one another, and to bring back the upper segment and the rear segment resiliently into the inactive position.

The prosthesis for at least one portion of a lower limb of a human, which prosthesis is equipped with an orthopaedic device according to the invention, is, advantageously and in accordance with the invention, chosen from among the prostheses for a lower limb of a human (prostheses for the foot or prostheses for the foot and leg especially) which are adapted to make possible movements of plantar flexion and movements of dorsiflexion about the axis of the ankle (that is to say, about the bi-malleolar axis). A prosthesis of this kind also preferably has a mechanical strength which is adapted to make possible at least partly vertical support of the weight of the body of the person wearing the prosthesis. The mobility of a prosthesis of this kind is therefore very similar to that of a lower limb of a human, thus allowing any movement which is normally made possible by a lower limb, especially any movement associated with walking or running, and at the same time having strength like that of a living human leg and foot. In order to accomplish this, it is not essential to use an electronically controlled prosthesis, since a prosthesis that allows the movements normally made possible by a lower limb of a human is sufficient.

The invention also relates to a method of manufacturing an orthopaedic device according to the invention.

An orthopaedic device according to the invention may be manufactured by any method for utilising and preparing composite materials with a polymeric matrix. In particular, an orthopaedic device according to the invention may be manufactured by any moulding process, for example by contact moulding onto an impression or by moulding with the aid of textiles pre-impregnated with a polymeric matrix. The method of manufacturing an orthopaedic device according to the invention may comprise a stage comprising polymerisation under vacuum and/or under pressure. An orthopaedic device according to the invention may also be manufactured by a method comprising the infusion or injection of liquid polymeric resin. In order to accomplish this, it is possible to use a mould which is representative of a foot or a lower limb of a human.

The invention also relates to an orthopaedic device, a shoe and a method of manufacture which are characterised, in combination, by all or some of the features which are mentioned above or below.

BRIEF DESCRIPTION OF THE DRAWINGS

Other aims, features and advantages of the invention will become apparent on reading the following description of one of its modes of preferred embodiment, which is given as a non-limitative example and which refers to the appended drawings, in which.

DETAILED DESCRIPTION OF THE PREFERRED EMBODIMENTS

Figure 1:
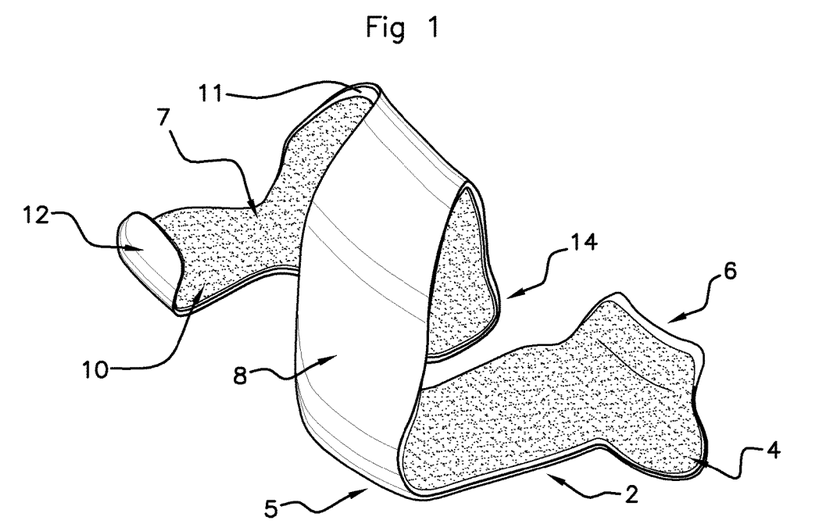
FIG. 1 is a diagrammatic view in perspective of a first mode of embodiment of an orthopaedic device according to the invention.
Figure 2:
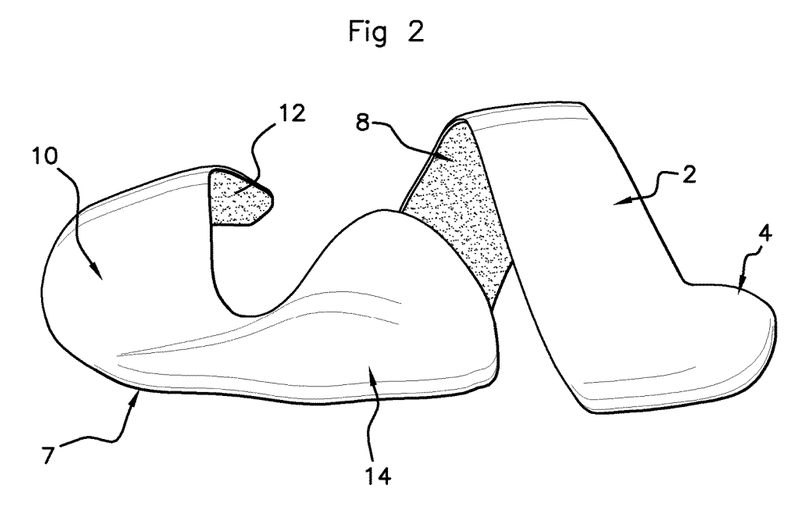
FIG. 2 is a diagrammatic view from below of a first mode of embodiment of an orthopaedic device according to the invention.

According to a first mode of embodiment according to the invention, which is represented in FIGS. 1 and 2, the orthopaedic device is a pedal brace (or orthosis) which is in the form of a wound ribbon which is helical overall and comprises an outer layer of a rigid material, providing a recess for a foot, in such a way that the ribbon has the appearance of being wound round the foot from the forefoot to the heel.

The pedal brace according to the invention which is represented in FIGS. 1 and 2 is adapted to receive a human right foot.

The outer layer of the pedal brace represented in FIGS. 1 and 2 is formed from an epoxy resin within which there extend, as reinforcement, carbon fibres, for example in the form of two or three layers of a serge-like or taffeta textile, preferably a non-unidirectional one.

The ribbon forming the brace has a thickness such that it is possible to wear it inside a shoe. The thickness of the material forming the brace (apart from the thickness of any layer of padding material) is, for example, between 0.2 mm and 5 mm, and especially between 0.5 mm and 2 mm. The ribbon forming the brace has, for example, an average width of between 1 cm and 7 cm, and especially between 1.5 cm and 4 cm.

At the front of the foot, on the inner side of said foot (where the big toe is located), the brace is adapted to extend between an inner lateral border 6, which is adapted to support the big toe of the foot laterally, and an outer lateral edge 5 which is adapted to receive the fifth metatarsus of the foot, thus forming a front segment 2.

The front segment 2 therefore extends in the form of a first plate, between a lateral edge, which is adapted to receive the big toe, and the outer lateral edge 5 which is adapted to receive the fifth metatarsus of the foot. The front segment is adapted to extend over the entire width of the forefoot and to provide optimum support for said forefoot, in this instance support for each of the five metatarsi.

The front segment 2 has a front appendage 4 which is adapted to receive the big toe. Said front appendage 4 is adapted to be disposed opposite the lower face of the big toe of the foot. Said big toe (or hallux) rests at least partially on the front appendage 4 of the front segment 2 when the person wearing the brace is standing upright, resting on his/her foot, or during the supporting phases of walking or running.

On the outer side at the front of the foot, where the little toe (or quintus) is located, the outer lateral edge 5 of the front segment 2 of the brace is prolonged upwards, above the foot, in the form of an upper arch 8 which is rigid but is resilient in flexion. The upper arch 8 is formed from a portion of the said ribbon which is wound round on itself and which extends as far as the inner malleolar region of the foot and is prolonged under the heel, thus forming a rear segment 10. The upper arch 8 extends obliquely, in contact with the upper face of the foot, between an outer lateral end of the front segment 2 and an inner lateral end 7 of the rear segment 10. The upper arch 8 thus forms a recess into which a foot can be introduced, at least in the inactive position, after the manner of a shoe.

The rear segment 10 extends in the form of a second plate, between an inner lateral end and an outer lateral border 12, in such a way as to extend under the entire width of the heel and to support the latter.

The upper arch 8 has an inner appendage 14 which is adapted to at least partially support the arch of the foot. The inner appendage 14 of the upper arch 8 is disposed on the inner side of the foot and extends laterally and under the foot, thus forming an inner arch which is adapted to follow the curvature of the arch of the foot.

The front segment 2 and the rear segment 10 thus constitute two supports for the foot, for the forefoot and heel respectively. These two segments are connected by the rigid upper arch 8 which is resilient in flexion and is adapted, on the one hand, to keep the front segment 2 and the rear segment 10 in an inactive position and, on the other hand, to make possible a relative displacement of the front segment 2 and the rear segment 10 in relation to one another, starting from the inactive position, and to bring them back resiliently into said inactive position. The inactive position of the brace according to the invention is substantially the same, whether on its own or with a foot inserted in it. The inactive position of the brace corresponds, in particular, to a normal position of the foot and the leg, for example when standing up.

The pedal brace according to the invention is adapted to be in contact with the foot, or possibly to adjust itself in such a way as to come into contact with the foot, especially in the inactive position. A brace of this kind is easy to put on by simply slipping the foot inside the recess for receiving the foot provided by the front segment 2, the rear segment 10 and the upper arch 8.

The upper arch 8 makes it possible for the front segment 2 and the rear segment 10 to be displaced in relation to one another, both in the longitudinal direction of the foot and in a direction perpendicular to said longitudinal direction of the foot. The brace is thus adapted to accompany all the displacements of the forefoot and heel, especially when walking or running.

The upper arch 8 is adapted not only to make possible a relative displacement of the front segment 2 and the rear segment 10 in relation to one another, starting from the inactive position, but also to bring back said front segment 2 and said rear segment 10 resiliently into the inactive position.

The upper arch 8 connecting the front segment 2 and rear segment 10 thus acts after the manner of a spring or of a bow which restores the potential energy, which is stored up during the elastic deformation of said upper arch 8 when the front segment 2 and the rear segment 10 are displaced from the inactive position, in the form of kinetic energy which makes possible a dynamic effect for lifting the forefoot and an effect for propelling the heel at the end of the step.

The brace therefore makes it possible to facilitate walking by keeping the foot in an anatomically correct position, but also by providing a propulsive effect at the end of the step. When walking, the propulsive effect manifests itself, in particular, at the end of the supporting phase, when the heel is raised and when only the forefoot and toes still remain in contact with the ground. The front segment 2 and the rear segment 10 are then displaced in relation to one another, out of the inactive position, and the upper arch 8 is tensioned. The resilient potential energy stored up by the brace during the forward flexion of the leg which accompanies this stage of walking is then restored, thus producing, at the end of the step, an effect which propels the foot forwards when the toes are no longer resting on the ground.

Furthermore, the brace also makes it possible to support the arch of the foot effectively, especially during the forward flexion of the leg and when the heel is raised. In actual fact, the tensioning of the brace also brings about a tensioning of the inner appendage 14 forming a support for the arch of the foot, and makes it all the more possible to keep the arch of the foot in position and prevent it from sagging.

Moreover, for the sake of greater comfort, a thin film 11 made of cellular material such as a synthetic foam is disposed on, and stuck to, the inner surface of the brace, that is to say the surface which is intended to be in contact with the foot.

Figure 3:
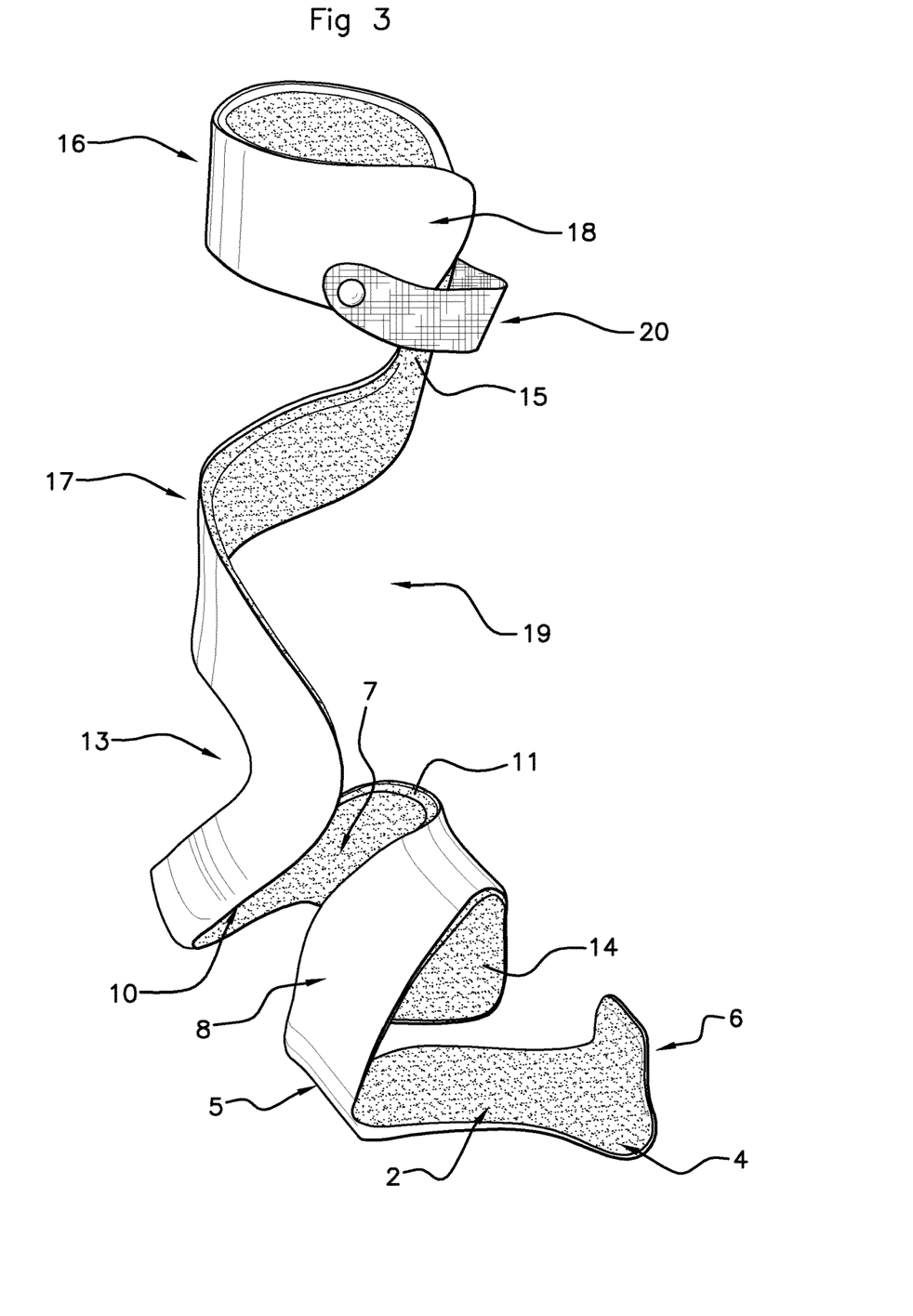
FIG. 3 is a diagrammatic view in perspective of a second mode of embodiment of an orthopaedic device according to the invention, which also comprises a leg part.

According to a second mode of embodiment, which is represented in FIG. 3, of an orthopaedic device according to the invention, the latter is a pedal brace which is in the form of a helical ribbon formed from a rigid material and provides a recess for a lower right-hand limb of a human, in such a way that the ribbon has the appearance of being wound round the foot from the forefoot as far as the heel and then round the calf as far as a point below the knee.

The pedal brace according to the invention which is represented in FIG. 3 has a lower part, which forms a recess for the foot, and an upper part which forms a recess for the leg. The lower part of this second mode of embodiment of the brace is identical to the brace according to the first mode of embodiment which is described above and represented in FIGS. 1 and 2. However, the outer lateral border of the rear segment 10 is not discontinued at the outer malleolus but is prolonged, thus forming the upper part of the brace.

The upper part of the brace is formed from an upper segment 19 which is adapted to extend in contact with at least part of the leg which is wearing the brace, and in particular to extend at least partially in contact with the front outer compartment of the leg, thus forming a support for the front face of the leg.

The upper segment 19 comprises a curved first part 13 which extends upwards from the rear segment 10 of the lower part of the brace in such a way as to form a support which is in contact with the front outer compartment of the leg. Said first part 13 assumes the shape of an arc of a circle which extends from the outer malleolus to halfway up the calf. It is prolonged into a second part 17 of the upper segment 19, which extends to the rear and round the calf. Said second part 17 then extends upwards, thus forming a third part 15 of the upper segment 19. Said third part 15 forms an arc of a circle which extends upwards on the inner side of the calf. Below the knee, the third part 15 is prolonged into a fourth part 16 which extends to the rear and round the top of the calf as far as a fifth part 18, thus forming a ring which is open at the front of the leg. Said fifth part 18 has an upper terminal edge to which a tie with a flexible self-gripping ribbon 20 is fastened.

At the third part 15, there is fastened a loop through which the flexible self-gripping ribbon 20 can be passed in such a way as to form an opening/closing device.

The upper segment 19 makes it possible to improve the maintenance of the lower limb in position by reinforcing the effect that keeps the foot in position. The support formed by the upper segment 19 around the leg which is wearing the brace makes it possible to improve the effect that lifts the forefoot of the brace and to amplify the propulsive effect, which is provided by means of the pedal brace, at the end of the step. The upper segment 19 also makes it possible to improve the effect for stabilising the foot and the leg laterally, by helping to keep the leg and foot in position in the same sagittal plane, but without impeding lateral movements of the leg in relation to the foot.

A brace according to this second mode of embodiment makes it possible to facilitate walking not only by keeping the foot and the leg in an anatomically correct position, but also by providing a propulsive effect at the end of the step. The propulsive effect is further amplified compared to the first mode of embodiment of a brace according to the invention (that is to say with an upper part), since the first part 13 and fifth part 18 of the said upper segment 19 form front outer and front supports and the second part 17 and fourth part 16 of the said upper segment 19 form rear supports, the whole arrangement also making it possible to tension the brace and to provide an improved propulsive effect for the leg and the foot at the end of the step.

A pedal brace such as a brace according to this second mode of embodiment is easy to put on, for example by first slipping the foot inside the recess for receiving the foot provided by the front segment 2, the rear segment 10 and the upper arch 8, while at the same time keeping the upper part towards the rear or the outside with one hand and then bringing the upper part back around the leg.

A synthetic foam in the form of a thin film 11 made of cellular material is stuck to that inner surface of the brace which is intended to come into contact with the foot and the leg, in the event of the brace being used inside a shoe. The synthetic foam is advantageously chosen from among the synthetic foams which are suitable for coming into contact with the human skin (in particular non-allergenic foams).

Figure 4:
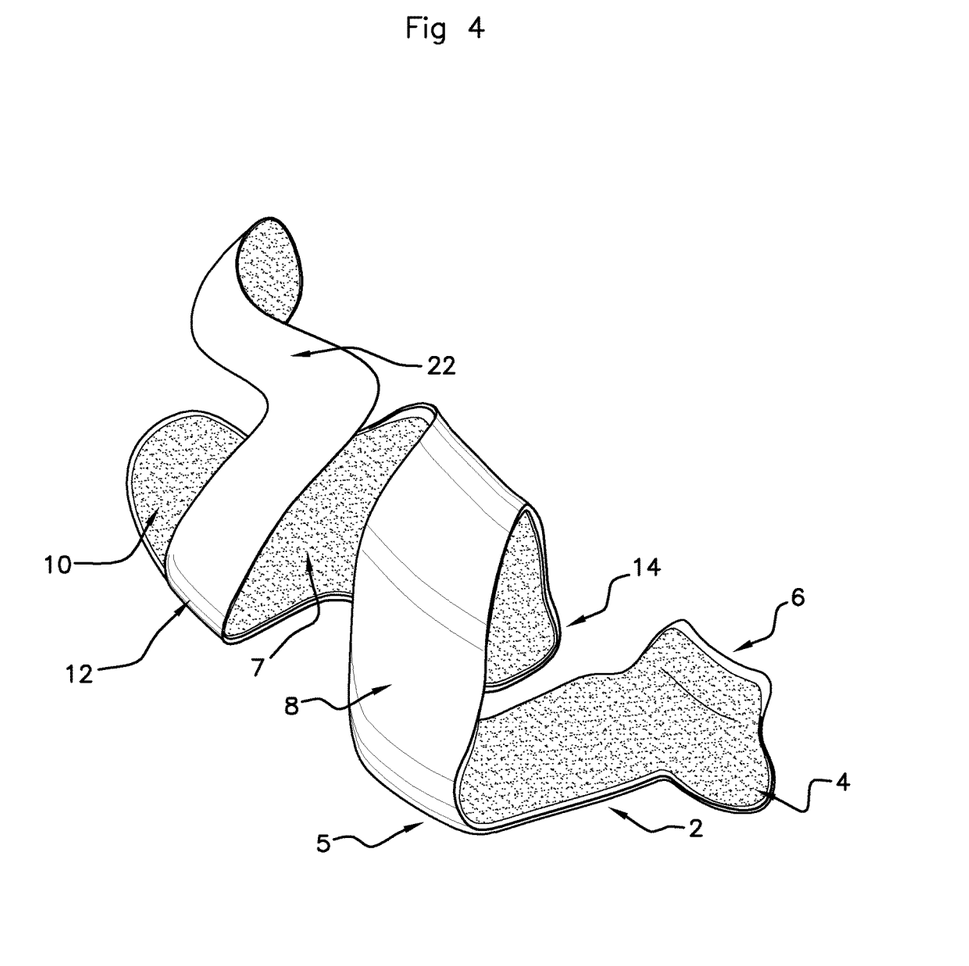
FIG. 4 is a diagrammatic view in perspective of a third mode of embodiment of an orthopaedic device according to the invention.

According to a third mode of embodiment, which is represented in FIG. 4, of an orthopaedic device according to the invention, the latter is a pedal brace which is in the form of a helical ribbon formed from a rigid material and provides a recess for a foot, such as a brace according to the first mode of embodiment represented in FIGS. 1 and 2, but is prolonged from the outer lateral border 12 to the front of the ankle by a portion 22 which is adapted to be in contact with the instep. The ribbon therefore has the appearance of being wound round the foot from the forefoot as far as the heel and then over the top of the foot at the instep.

The upper arch 8 has an inner appendage 14 which is adapted to at least partially support the arch of the foot. In one particularly advantageous mode of embodiment, the inner appendage may also be in the form of an elastic textile which is adapted to extend under the arch of the foot and to form a support for said arch of the foot.

A brace according to the third mode of embodiment may, for example, be used on its own or in a high shoe, such as a walking or hiking shoe.

In the event of a shoe being equipped with the brace, said brace may be disposed in the shoe in such a way as to be detachable, or else may be fastened in the latter, for example by a seam between an edge of the resilient textile forming the inner appendage which supports the arch of the foot.

In this way, wearing such a brace makes it possible to facilitate walking, both by keeping the foot in an anatomically correct position and by providing a propulsive effect at the end of the step. This propulsive effect at the end of the step is especially improved owing to the front support formed by the portion 22 of the brace at the instep. During walking, therefore, at the end of the supporting phase, when the heel is raised and when only the forefoot and the toes still remain in contact with the ground, the front segment and the rear segment are displaced in relation to one another out of the inactive position, and the upper arch is tensioned. The portion 22 of the brace at the instep is also displaced forwards as a result of the ankle bearing on it, and contributes to tensioning the brace. The potential energy stored up by the brace in the course of this forward flexion of the leg is then subsequently restored, thus producing, at the end of the step, an effect that propels the foot forwards when the toes are no longer resting on the ground.

The portion 22 of the brace may also be prolonged towards the rear of the ankle in such a way as to keep the foot in position more satisfactorily.

Furthermore, during the forward flexion of the leg (heel raised), the tensioning of the brace also brings about a tensioning of the inner appendage forming a support for the arch of the foot, and makes it all the more possible to keep the arch of the foot in position and prevent it from sagging, in particular during this phase of walking (leg bent, heel raised and forefoot resting on the ground).

A brace according to this third mode of embodiment of an orthopaedic device according to the invention may advantageously be worn or be integrated into a shoe which rises above the ankle, such as a sports or hiking shoe or any other orthopaedic shoe. Said brace provides an improved propulsive effect, compared to a brace according to the first mode of embodiment, owing to the front support at the instep formed by the portion 22 of the brace. A brace of this kind thus makes it possible to facilitate walking and to make easier the efforts to be expended during a physical activity such as running or hiking.

Figure 5:
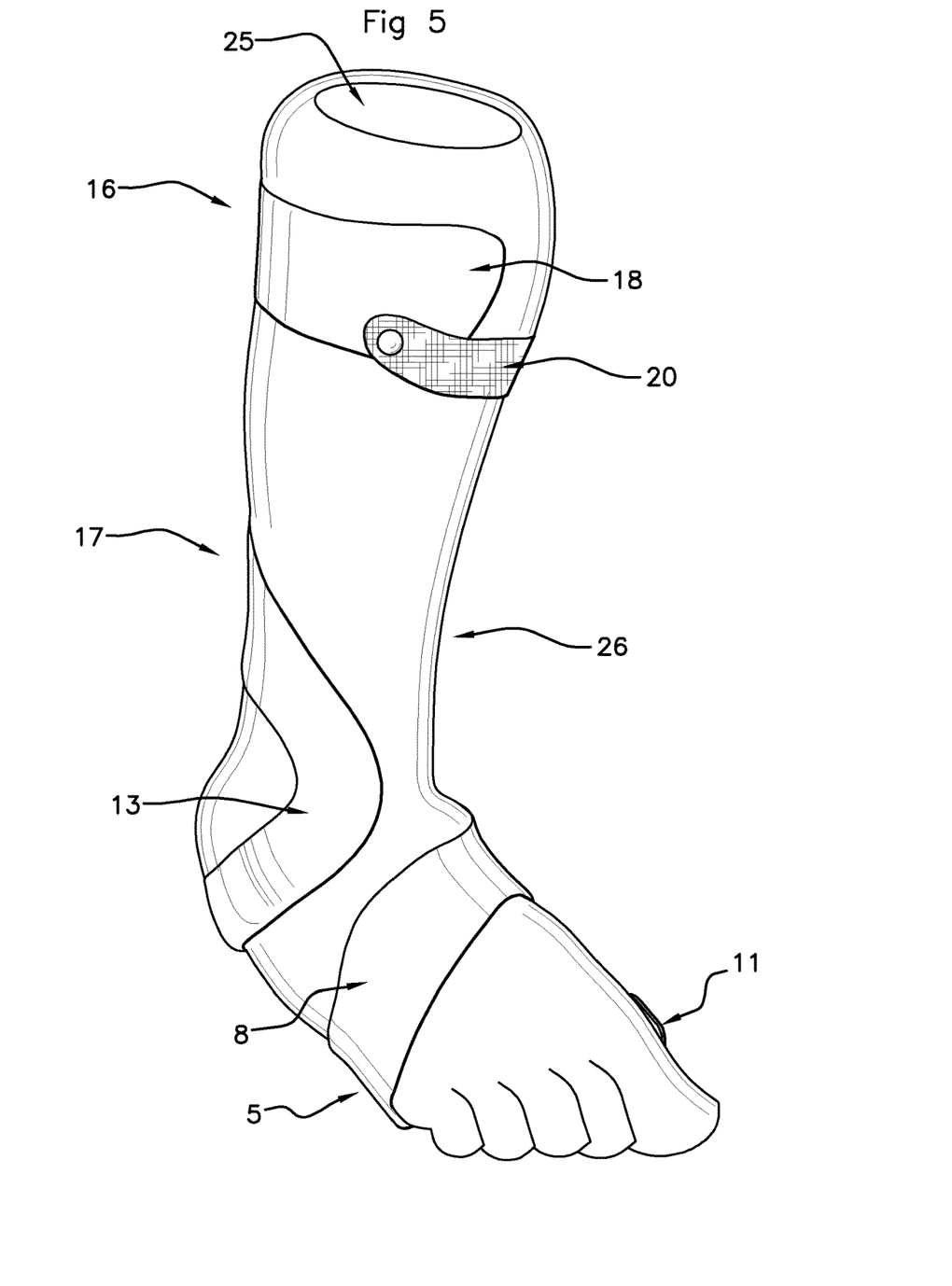
FIG. 5 is a diagrammatic view in perspective of a fourth mode of embodiment of an orthopaedic device according to the invention, comprising a leg part.

According to a fourth mode of embodiment, which is represented in FIG. 5, of an orthopaedic device according to the invention, said orthopaedic device is in the form of a prosthesis. In this mode of embodiment, a brace according to the second mode of embodiment, such as is represented in FIG. 3, is associated with a prosthesis 26 for a lower limb. A brace such as is represented in FIG. 3 is thus integrated as a blade into a lower limb prosthesis by simultaneous moulding or adhesion, or is simply disposed around or inside said prosthesis. The appearance and mobility of the prosthesis 26 (especially the mobility of the ankle joint) are very similar to those of a lower limb of a human. The prosthesis 26 also has a strength like that of a living leg and foot. The lower limb prosthesis 26 comprises an upper end 25 which can be fixed to a tibial stump. In particular, the prosthesis 26 makes possible movements of plantar flexion and of dorsification about the bi-malleolar axis, while at the same time having a strength which is similar to that of a living leg and foot.

A prosthesis according to this fourth mode of embodiment therefore makes it possible, apart from replacing a lower limb of a human, to provide stabilisation of the lower limb, and the maintenance of the latter in position, as well as an effect that lifts the forefoot and a propulsive effect at the end of the step, while at the same time leaving free the physiological ranges of motion of the various joints of the lower limb.

In this fourth mode of embodiment of an orthopaedic device according to the invention, the thin film 11 of synthetic foam is not necessary. Furthermore, since the brace according to the second mode of embodiment of the invention is, for example, integrated into the prosthesis 26, there is not necessarily any point in providing a device for opening/closing by means of a self-adhesive ribbon 20.

The orthopaedic devices according to the invention represented in FIGS. 1, 2, 3, 4 and 5 are adapted to receive a right foot and/or a right leg. Of course it is possible to produce any orthopaedic device according to the invention for a right foot as for a left foot (by symmetry).

The invention may form the subject of numerous variants of embodiment. In particular, the brace may be used outside a shoe (without, in this case, needing an inner layer of padding material), or even on its own (neither inside nor outside a shoe). Moreover, the same person may, as applicable, wear an orthopaedic device according to the invention on just one foot or an orthopaedic device according to the invention on each foot.

The invention claimed is:

1. An orthopaedic device for a lower limb of a human comprising:
    a front segment which is adapted to receive a sole of a forefoot of a foot, said front segment being formed from a first plate;
    a rear segment which is adapted to receive a lower face of a heel of said foot, said rear segment being formed from a second plate which is longitudinally spaced from the first plate such that the first plate and the second plate are distinct;
    wherein:
    said front segment and said rear segment are formed from two pieces which are distinct from one another;
    said front segment and said rear segment are connected by at least one upper arch that is resilient in flexion, and which:
    extends above said front segment and said rear segment, providing a recess for receiving said foot;
    is adapted to keep said front segment and said rear segment in an inactive position; and
    is adapted to make possible a relative displacement of said front segment and said rear segment in relation to one another, starting from the inactive position, and to bring back said front segment and said rear segment resiliently into the inactive position providing a propulsive dynamic effect, said upper arch exerting a force for bringing back said front segment and said rear segment into said inactive position.

2. The device according to claim 1, wherein said front segment and said rear segment extend in a longitudinal prolongation of one another and are longitudinally spaced apart from one another, at least in the inactive position.

3. The device according to claim 2, wherein said upper arch is adapted to make possible a relative displacement of said front segment and said rear segment in relation to one another, starting from the inactive position, in a sagittal plane.

4. The device according to claim 1, wherein said front segment is adapted to receive a big toe of said foot.

5. The device according to claim 1, wherein said upper arch extends between an outer lateral end of said front segment and an inner lateral end of said rear segment.

6. The device according to claim 1, wherein said front segment extends transversely between an inner lateral edge which is adapted to receive a big toe of said foot and an outer lateral edge which is adapted to receive a fifth metatarsus of said foot.

7. The device according to claim 1, wherein said rear segment extends transversely between an inner lateral end and an outer lateral border.

8. The device according to claim 1, wherein said upper arch has an inner appendage which extends laterally and downwards and is disposed longitudinally between said front segment and said rear segment in such a way as to form a support for an arch of said foot.

9. The device according to claim 1, wherein said front segment has an inner lateral border which is adapted to support a big toe of said foot laterally.

10. The device according to claim 1, wherein it comprises an upper segment which:
    extends above said rear segment, providing a recess for receiving a leg; and
    has:
      at least one portion which is adapted to form a front support which is in contact with a front compartment of said leg, and
      at least one portion which is adapted to form a rear support which is in contact with a rear compartment of said leg,
    said upper segment being connected resiliently to said rear segment in such a way as to:
    keep said rear segment in the inactive position;
    make possible a relative displacement of said upper segment and said rear segment in relation to one another, and to bring back said upper segment and said rear segment resiliently into the inactive position.

11. The device according to claim 1, wherein said device is formed from at least one composite material comprising at least one reinforcement in a form of fibers and at least one polymeric material within which said fibers extend.

12. A prosthesis for at least one portion of a lower limb of a human, wherein said prosthesis is equipped with an orthopaedic device according to claim 1.

13. The device according to claim 1, wherein,
    the first plate extends between i) a first lateral edge shaped to receive a big toe of said foot, and ii) an outer second lateral edge shaped to receive a fifth metatarsus of said foot,
    the first plate is shaped to extend over an entire width of the forefoot of said foot and to provide support for said forefoot, including support for each of five metatarsi,
    the first plate includes a front appendage shaped to receive the big toe of said foot, with said front appendage disposed opposite a lower face of the big toe of said foot so that said big toe rests at least partially on the front appendage of the first plate when a person wearing the device is standing upright,
    the at least one upper arch is connected to the outer second lateral edge of the first plate, the at least one upper arch being prolonged upwards from the first plate,
    the second plate extends between i) an inner first lateral end and ii) an outer second lateral border thereby to extend under an entire width of the heel of said foot and to support the heel of said foot,
    the at least one upper arch is connected to the inner first lateral end of the second plate, and
    the at least one upper arch includes an inner appendage is shaped to at least partially support an arch of said foot with the inner appendage of the upper arch disposed on the inner side of the foot and extending laterally and under the foot, thus following a curvature of the arch of the foot.

* * * * *